United States Patent [19]

Madou et al.

[11] Patent Number: 5,134,042
[45] Date of Patent: * Jul. 28, 1992

[54] SOLID COMPOSITIONS FOR FUEL CELLS, SENSORS AND CATALYSTS

[75] Inventors: Marc J. Madou, Palo Alto; Takaaki Otagawa, Fremont; Arden Sher, Foster City, all of Calif.

[73] Assignee: SRI International, Menlo Park, Calif.

[*] Notice: The portion of the term of this patent subsequent to Jul. 25, 2006 has been disclaimed.

[21] Appl. No.: 365,910

[22] Filed: Jun. 14, 1989

Related U.S. Application Data

[62] Division of Ser. No. 935,289, Nov. 26, 1986, Pat. No. 4,851,303.

[51] Int. Cl.$^5$ .............................. H01M 8/10
[52] U.S. Cl. ...................... 429/13; 429/33; 204/426
[58] Field of Search ................. 429/13, 33, 191; 204/426; 252/62.2

[56] References Cited

U.S. PATENT DOCUMENTS 4,402,924 9/1983 McVicker et al. ................ 423/258
(List continued on next page.)

FOREIGN PATENT DOCUMENTS 0194380 9/1986 European Pat. Off. .
(List continued on next page.)

OTHER PUBLICATIONS

Chemistry Letters, 1984, The Chemical Society of Japan (JP), S. Kuwata et al.,: "A Potentiometric Oxygen Sencor Using LaF$_3$ single crystal operative at room temperature", pp. 981–982, see abstract.
(List continued on next page.)

Primary Examiner—Stephen Kalafut
Attorney, Agent, or Firm—Phillips, Moore, Lempio & Finley

[57] ABSTRACT

The present invention relates to solid materials for use as electrolyte for a fuel cell, or for a sensor, or as a catalyst. Representative structures include lanthanum fluoride, lead potassium fluoride, lead bismuth fluoride, lanthanum strontium fluoride, lanthan strontium lithium fluoride, calcium uranium, cesium fluoride, PbSnF$_y$, KSn$_2$F$_4$, SrCl$_2$.KCl, LaOF$_2$, PbSnF$_8$.PbSnO, lanthanum oxyfluoride, oxide, calcium fluoride, SmNdFO, and the like. In another aspect, the present invention relates to a composite and a process to obtain it of the formula:

$$A_{1-y}B_yQO_3$$

having a perovskite or a perovskite-type structure as an electrode catalyst in combination with:

$$A_yB_{1-y}F_{2+y}$$

as a discontinuous surface coating solid electrolyte solid electrolyte wherein A is independently selected from lanthanum, cerium, neodymium, praseodymium, and scandium, B is independently selected from strontium, calcium barium or magnesium, Q is independently selected from nickel, cobalt, iron or manganese, and y is between about 0.0001 and 1, which process comprises:
(a) obtaining a particulate of:

$$A_{1-y}B_yQO_3$$

wherein A, B and y are defined hereinabove having an average size distribution of between about 50 and 200 Angstroms in diameter;
(b) reacting the particle of step (a) with a vapor comprising:

$$A_yB_{1-y}F_{2+y}$$

wherein A, B and y are defined hereinabove, at about ambient pressure at between about 0° and 1000° C.: for between about 10 and 30 hr. obtain a composite of between about 25 to 1000 microns in thickness;
(c) recovering the composite of step (b) having multiple interfaces between the electrode and electrolyte.

In another aspect the invention relates to the heating of these solid materials with oxygen and water to obtain higher ionic conductivity. In another aspect the invention relates to the electrochemical doping of oxide ions present by treatment of the electrode-lanthanum fluoride interface at between about 0° and 400° C. in an oxygen environment at between about 10$^{-3}$ and 10$^{-6}$ amperes per square centimeter for between about 1 and 60 minutes.

The invention also includes the use of the fuel cells disclosed to generate electricity.

17 Claims, 6 Drawing Sheets

U.S. PATENT DOCUMENTS 4,851,303  7/1989  Madou et al. ..................... 429/13

FOREIGN PATENT DOCUMENTS 1442686  4/1969  Fed. Rep. of Germany.
3112739  10/1982  Fed. Rep. of Germany.
2330127  5/1977  France.
2403652  4/1979  France.
2002739  2/1979  United Kingdom.

OTHER PUBLICATIONS

Patent Abstracts of Japan, vol. 10, No. 324 (P-512) (2380), Nov. 5, 1986 & JP, A, 61132855 (Shimadzu Corp), Jun. 20, 1986, see abstract.

Journal of the Electrochemical Society, vol. 120, No. 12, Dec. 1973, B. C. LaRoy et al.: "A solid-state electrode for reducible gases", pp. 1668–1673, see abstract; p. 1668, left-hand column, paragraphs 1, 3 cited in the application.

Journal of the Electrochemical Society, vol. 120, No. 2, Dec. 1973, A. C. Lilly et al.: "Transport properties of $LaF_3$ thin films", pp. 1673–1676, see p. 1673, left-hand column, paragraph 1.

Solid State Ionics, vol. 1, 1980, North Holland Publishing Company (NL), J. Schoonman et al.: "Solid electrolyte properties of $LaF_3$", pp. 211–221, see p. 212, paragraph 3; p. 220, last paragraph cited in the application.

Solid State Ionics, vol. 13, 1984, Elsevier Science Publishers B.V. (Amsterdam, NL), A. Roos et al.: "Electronic conductivity in $La_{1-x}Ba_xF_{3-x}$ crystals", pp. 205–211, see abstract; p. 205, left-hand column, paragraphs 1,2; right-hand column, paragraphs 3, 4.

Solid State Ionics, vol. 2, No. 3, Jun. 1981, North-Holland Publishing Company (Amsterdam, NL), K. E. D. Wapenaar et al.: "Conductivity enhancement in fluorite-structured $Ba_{1-x}La_xF_{2+x}$ solid solutions", pp. 145–154, see abstract; p. 153, right-hand column, paragraph 2.

Solid State Ionics, vol. 6, No. 4, Jul. 1982, North-Holland Publishing Co. (Amsterdam, NL), P. O. Fedorov et al.: "Ionic conductivity in the single crystals of non-stoichiometric fluorite phases $M_{1-x}R_x$; $F_{2+x}$(M=Ca, Sr, Ba; R=Y, La–Lu)", pp. 331–335, see abstract.

Solid State Ionics, vol. 13, 1984, Elsevier Science Publishers B.V. (Amsterdam, NL), A. Roos et al.: "Ionic conductivity tysonite-type solid solutions in tysonite-type solid solutions $La_{1-x}Ba_xF_{3-x}$", pp. 191–203, see abstract; p. 191, left-hand column, #1; p. 200, left-hand column, lines 5–8.

Solid State Ionics, vol. 9/10, part 1, Dec. 1983, North-Holland Publishing Co. (Amsterdam, NL), J. A. Archer et al.: "Ionic conductivity studies of heavily rare earth doped fluorites", pp. 505–510, see p. 506, left-hand column, paragraph 2,3; right-hand column, last paragraph, p. 508, table I.

Solid State Ionics, vol. 15, 1985, North-Holland (NL), H. Geiger et al.: "Ionic conductivity single crystals of the nonstoichimetric tysonite phase $La_{(1-x)}Sr_xF_{(3-x)}(OxO, 14)$", pp. 155–158, see abstract.

C. R. Acad. Sc. Paris, vol. 276, #3, section C, Jan. 15, 1973, A. Pelloux et al., "Sur les propriétés de l'oxyfluorure de lanthane comme electrolyte solide", pp. 241–244, see p. 241, paragraph 1; p. 244, last paragraph.

Journal of the Electrochemical Society, vol. 129, #2, Feb. 1982, (Manchester, N.H., U.S.), H. S. Isaacs et al.: "Comparison of materials as oxygen catalytic electrodes on zirconia electrolyte", see pp. 436–443.

Chemical Abstracts, vol. 74, #14, Apr. 5, 1971 (Columbus, Ohio, U.S.), J. Vesely: "Crystals of lanthanum fluoride as the functioning layers of fluoride electrodes", see p. 508, abstract No. 70836d, & Chem Listy 1971, 65(1), 86–90.

Journal of the Electrochemical Society, vol. 124, No. 2, Feb. 1977, T. Takahashi et al.: "Ionic conductivity of doped cerium trifluoride", pp. 280–284, see abstract; p. 280, left-hand column, paragraph 4; p. 281, table I.

Kuwata et al., "A potentiometric oxygen sensor using $LaF_3$ single crystal operative at room temperature", *Chemistry Letters*, 1984, No. 6 (Jun.), pp. 981–982.

Chemical Abstracts, vol. 103, No. 8982, Jul. 15, 1985. Bockris et al., "The electrocatalysis of oxygen evolution on perovskites", J. Elect. Soc., vol. 131, No. 2, pp. 290–302, Feb. 1984.

FIGURE 1

Table 1. Fuel cell types

| | Phosphoric acid | Molten carbonate | Alkaline | High-temperature solid oxide | Solid polymer |
|---|---|---|---|---|---|
| Electrolyte | Conc. $H_3PO_4$ | $K_2CO_3$–$Li_2CO_3$ | KOH solution | $ZrO_2$–$Y_2O_3$ or $ZrO_2$–CaO | Sulfonated fluorocarbon acidic ion exchange membrane |
| Electrolyte support | Phenolic fiber (SiC) | $LiAlO_2$ | Asbestos | Electrolyte itself | Electrolyte itself |
| Electrode (catalyst) | Pt | Ni, NiO | Pt, Pt–Au alloy | NiO-$ZrO_2$–$La_{0.9}Sr_{0.1}MnO_3$ | Pt |
| Anode fuel | $H_2$ (reformer product) | $H_2$–CO | $H_2$ (high purity) | $H_2$–CO | $H_2$ |
| Cathode oxidant | Air | Air + $CO_2$ | $O_2$ (high purity) | Air | $O_2$ |
| Temperature (°C) | 160–190 | 600–700 | 82–104 | 900–1100 | 82 |
| Pressure (atm) | <120 psia | <120 psia | 60 psia | Atm | 60 psia |
| Cell voltage (V) | <0.8 | <0.85 | <0.97 | <0.90 | <0.95 |
| Impurity tolerance | <2000 ppm CO$^a$ <1 ppm $H_2S^a$ | No $H_2S$ | High-purity feeds, no CO and $CO_2$ | Not yet defined | Strict moisture control |
| Development status | Nearest to commercialization | Next nearest to commercialization | Apollo and Columbia space flights | Third-generation technology | Gemini space flights |
| Anode reaction | $H_2 \rightarrow 2H^+ + 2e^-$ | $H_2 + CO_3^{-2} \rightarrow H_2O$ (g) + $CO_2$ + $2e^-$ | $H_2 + 2OH^- \rightarrow 2H_2O$ (g) + $2e^-$ | $H_2 + O^{-2} \rightarrow H_2O$ (g) + $2e^-$ or CO + $O^{-2} \rightarrow CO_2 + 2e^-$ | $H_2 \rightarrow 2H^+ + 2e^-$ |
| Cathode reaction | $2e^- + \frac{1}{2}O_2 + 2H^+ \rightarrow H_2O$ | $CO_2 + \frac{1}{2}O_2 + 2e^- \rightarrow CO_3^{-2}$ | $H_2O + \frac{1}{2}O_2 + 2e^- \rightarrow 2OH^-$ | $\frac{1}{2}O_2 + 2e^- \rightarrow O^{-2}$ | $2H^+ + \frac{1}{2}O_2 + 2e^- \rightarrow H_2O$ |
| Overall reaction | $H_2 + \frac{1}{2}O_2 \rightarrow H_2O$ (g) | $H_2 + \frac{1}{2}O_2 \rightarrow H_2O$ (g) | $H_2 + \frac{1}{2}O_2 \rightarrow H_2O$ (l) | $H_2 + \frac{1}{2}O_2 \rightarrow H_2O$ (g) or CO + $\frac{1}{2}O_2 \rightarrow CO_2$ | $H_2 + \frac{1}{2}O_2 \rightarrow H_2O$ (l) |

OPEN CIRCUIT VOLTAGE ($V_{OC}$) vs. TIME CURVE for a SINGLE CRYSTAL $LaF_3$ SAMPLE upon an ON/OFF CYCLE of $H_2$. CATHODE: $Pt$/AIR; ANODE: $Pt$/$H_2$.

Pd/Pt system

FIGURE 5
Table 3.

| Reading | $V_{oc}$ | | | | $V_{oc}$(experimental) $=V_{oc}$(air)$-V_{oc}$(oxy.) | $V_{oc}$ from theory |
|---|---|---|---|---|---|---|
| | Air | $N_2$ | $O_2$ | $H_2$ | | |
| 1. | 100 | 134 | 72 | ---- | 28 | 9.8 |
| 2. | 112 | ---- | 80 | 800 | 32 | 9.8 |
| 3. | 151 | 223 | 140 | 800 | 11 | 9.8 |

FIGURE 7
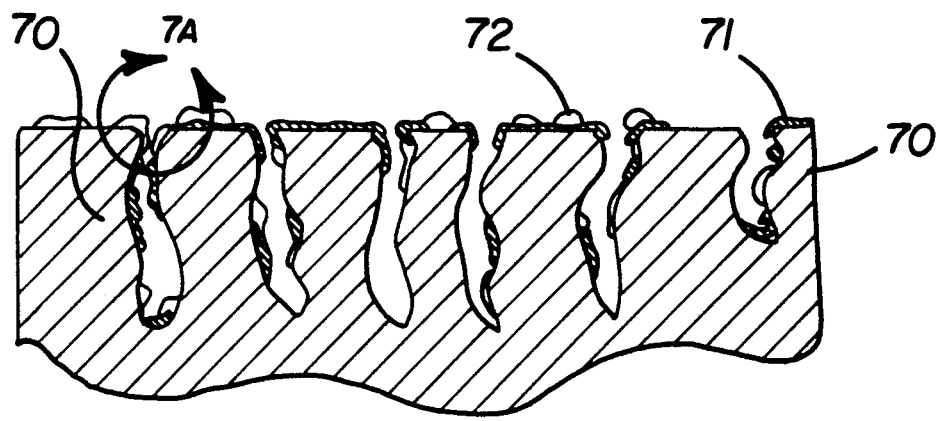
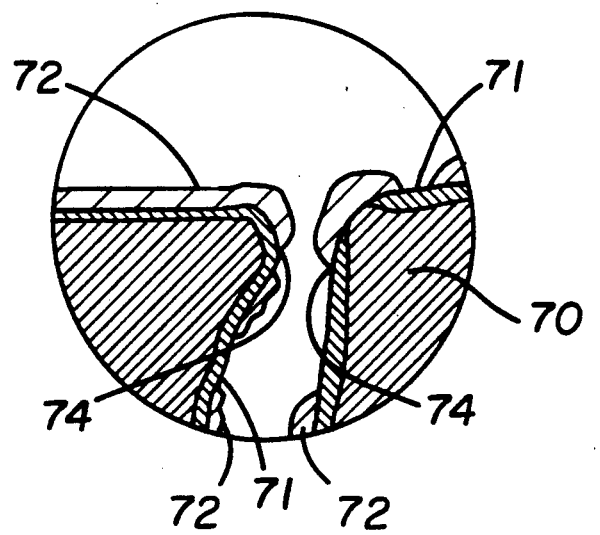
FIGURE 7A

SOLID COMPOSITIONS FOR FUEL CELLS, SENSORS AND CATALYSTS

This application is a division of Ser. No. 935,289, filed Nov. 26, 1986, now U.S. Pat. No. 4,851,303.

BACKGROUND OF THE INVENTION

1. Field of the Invention

The present invention relates to materials and processes to prepare polycrystal and monocrystal forms for use in fuel cells in sensors and as catalysts. In specific embodiments, a fuel cell having oxygen/solid lanthanum fluoride (as a single crystal)/hydrogen configuration produces about 1 volt of open circuit potential at essentially ambient temperature. In other specific embodiments, specific mixed lanthanide or alkaline earth fluorides also produce electricity at moderate temperatures. Embodiments also include a porous perovskite-type metallic transition metal oxide electrode and a lanthanum metal/alkaline earth/fluoride electrolyte which are useful as a solid electrode/electrolyte in a fuel cell, as a sensor, or as a catalyst.

2. Description of the Relevant Art

Fuel cells convert chemical energy to electrical energy directly, without having a Carnot-cycle efficiency limitation, through electrochemical oxidation-reduction reactions of fuels. Several types of fuel cells have been or are being investigated at the present time. These may generally be classified as shown in FIG. 1, as Table 1, depending upon the kinds of electrolyte used and the operation temperature.

The solid electrolyte fuel cell which can be considered as the third generation fuel cell technology, is essentially an oxygen-hydrogen (or $H_2$-CO mixture) fuel cell operated at high temperature (ca. 1000° C.) with a solid ceramic oxide material used as the electrolyte. At present, yttrium- or calcium-stabilized zirconium oxides have been used as the electrolyte. The mechanism of ionic conduction is oxygen ion transport via $O^{2-}$ anion in the solid oxide crystal lattice.

Additional references of interest include the following.

B. C. LaRoy et al., in the *Journal of the Electrochemical Society: Electrochemical Science and Technology*, Vol. 120, No. 12 pp. 1668-1673, published in December 1973, disclose some electrical properties of solid-state electrochemical oxygen sensors using vapor deposited thin films. Polycrystalline lanthanum fluoride solid electrolytes were investigated at ambient temperature.

T. Horiba in U.S. Pat. No. 4,550,067 discloses secondary cell batteries in which the positive electrode is made of materials such as phthalocyanine complexes, metal porphyrin complexes and the like.

Lyall in U.S. Pat. No. 3,625,769 and Fouletier in U.S. Pat. No. 4,526,674 each disclose lithium/oxygen fuel cells.

Raleigh in U.S. Pat. No. 4,118,194 and Weininger in U.S. Pat. No. 3,565,692, each disclose halogen electrochemical cells or the like.

Ledorenko in U.S. Pat. No. 4,172,022 and Eliot in U.S. Pat. No. 3,645,795, each disclose the use of phthalocyanine compounds in gas sensor electrodes.

Zeitner in U.S. Pat. No. 3,909,297 discloses a lithium-chloride battery.

In U.S. Pat. Nos. 3,698,955 and 3,719,564, Lilly discloses the use of rare earth fluorides such as lanthanum fluoride as solid electrolytes which are deposited as their films in a battery and a gas sensor respectively.

G. W. Mellors in European Patent Application No. 055,135 discloses a composition which can be used as a solid state electrolyte comprising at least 70 mole percent of cerium trifluoride and/or lanthanum trifluoride, an alkaline earth metal compound e.g. fluoride, and an alalki metal compound e.g. lithium fluoride.

Additional references cited also include the following.

B. V. Tilak, R. S. Yeo, and S. Srinivasan (1981), "Electrochemical Energy Conversion-Principles", in "Comprehensive Treatise of Electrochemistry" Vol. 3: Electrochemical Energy Conversion and Storage (J. O'M. Bockris et al. editors), pp. 39-122, Plenum Press, New York.

K. K. Ushiba, (1984), "Fuel Cells", Chemtech, May, pp. 300-307.

A. Sher, R. Solomon, K. Lee, and M. W. Muller (1967), "Fluorine Motion in $LaF_3$", in "Lattice Defects and Their Interactions", R. R. Hasiguti, Editor, pp. 363-405, Gordon and Breach Science Publishers, New York.

A. Yamaguchi and T. Matsuo (1981), "Fabrication of Room Temperature Oxygen Sensor Using Solid Electrolyte $LaF_3$ (Japanese)", Keisoku-Jidoseigyo-Gakkai Ronbunshu, Vol 17(3), pp. 434-439.

M. A. Arnold and M. E. Meyerhoff (1984), "Ion-Selective Electrodes," Anal. Chem., Vol. 56, 20R-48R.

S. Kuwata, N. Miura, N. Yamazoe, and T. Seiyama (1984), "Potentiometric Oxygen Sensor with Fluoride Ion Conductors Operating at Lower-Temperatures (Japanese)", J. Chem. Soc. Japan., 1984(8), pp. 1232-1236, and "Response of A Solid-State Potentiometric Sensor Using $LaF_3$ to A Small Amount of $H_2$ or CO in Air at Lower Temperatures", Chemistry Letters, pp. 1295-1296, 1984.

M. Madou, S. Gaisford, and A. Sher (1986), "A Multifunctional Sensor for Humidity, Temperature, and Oxygen", Proc. of the 2nd International Meeting on Chemical Sensors, Bordeaux, France, pp. 376-379.

A. McDougall (1976), "Fuel Cells", Energy Alternatives Series (C. A. McAuliffe, series editor), The Macmillan Press Ltd., London.

T. Takahashi (1984), "Fuel Cells (Japanese)", Chemistry One Point Series 8 (M. Taniguchi, editor), Kyoritsu-shuppan, Tokyo, Japan.

N. Yamazoe, N., J. Hisamoto, N. Miura, S. Kuwata (1968), "Solid State Oxygen Sensor Operative at Room Temperature", in Proc. of the 2nd Int. Meeting on Chemical Sensors, Bordeaux, France.

J. Meuldijk, J. and H. W. den Hartog (1983), "Charge Transport in $Sr_{1-x}La_xF_{2+x}$ solid solutions. An Ionic Thermocurrent Study", Physical Review B, 28(2), pp. 1036-1047.

H. W. den Hartog, K. F. Pen, and J. Meuldijk (1983), "Defect Structure and Charge Transport in Solid Solutions $Ba_{1-x}La_xF_{2+x}$", Physical Review B, 28(10), pp. 6031-6040.

J. Schoonman, J., G. Oversluizen, and K. E. D. Wapenaar (1980), "Solid Electrolyte Properties of $LaF_3$", Solid State Ionics, Vol. 1, pp. 211-221.

A. F. Aalders, A. Polman, A. F. M. Arts and H. W. de Wijn (1983), "Fluorine Mobility in $La_{1-x}Ba_xF_{3-x}$ ($0<x<0.1$) Studied by Nuclear Magnetic Resonance", Solid State Ionics, Vol. 9 and 10, pp. 539-542.

A. K. Ivanovshits, N. I. Sorokin, P. P. Fedorov, and B. P. Sobolev (1983), "Conductivity of $Sr_{1-x}Ba_xF_{3-x}$ Solid Solutions with Compositions in the Range $0.03 \leq x \leq 0.40$," Sov. Phys. Solid State, 25(6), pp. 1007-1010.

J. O'M. Bockris, and T. Otawaga (1984), "The Electrocatalysis of Oxygen Evolution on Perovskites", J. Electrochemical. Soc., 131(2), pp. 290-302.

Additional general information is found in "Fuel Cells" by E. J. Cairns et al. in *Kirk-Othmer: Encyclopedia of Chemical Technology*, (3rd Ed.), Vol. 3, pp. 545-568; and in "Fuel Cells" by O. J. Adlhart in *Van Nostrand's Scientific Encyclopedia*, 6th ed., D. M. Considine (ed), Van Nostrand Reinhold Co., New York, pp. 1296-1299, 1986, which are both incorporated herein by reference.

Solid electrolyte fuel cells have several advantages over the other types of fuel cells:
1. There are no liquids involved and, hence, the problems associated with pore flooding, maintenance of a stable three-phase interface, and corrosion are totally avoided.
2. Being a pure solid-state device, it poses virtually no maintenance problems. For example, the electrolyte composition is invariant and independent of the composition of the fuel and oxidant streams.
3. Inexpensive metallic oxides (ceramics) rather than expensive platinum can be used as the electrode catalysts.
4. The solid electrolyte fuel cells demand less feed gas preparation than the phosphoric acid cell (see FIG. 1), which requires a conversion of CO to $H_2$ via the water-gas shift reaction, or the molten carbonate cell (see FIG. 1), which requires a carbon dioxide loop due to the use of carbonate ions for ionic transport.

The attraction of developing a solid electrolyte fuel cell is its simplicity. However, a high operation temperature (ca. 1000° C.) is by far the most critical aspect of this type of fuel cell. Although high operation temperature produces high-quality exhaust heat that can generate additional electrical power, leading to a high overall system efficiency, maintaining the integrity of the cell components such as the interconnector is the most difficult challenge.

It is therefore desirable to develop alternative low temperature solid materials and composites for use as solid electrolytes in fuel cells, as solid sensors and as solid catalysts that can be operated in a range of 400°-600° C. or lower (preferably about 200° C., especially at ambient temperature). Some of the structures described herein have been examined for usefulness as battery electrolytes. However, none of the references cited hereinabove, individually or collectively, disclose or suggest the present invention as described herein. The present invention relates to the design of such low temperature solid electrolyte fuel cells, sensors, or catalysts based on non-oxide solid electrolytes, such as solid solutions of lanthanide fluorides (e.g. $La_xSr_{1-x}F_{2+x}$).

SUMMARY OF THE INVENTION

The present invention relates to solid materials which have application as an electrolyte for a fuel cell, a sensor or a catalyst. More specifically, the present invention relates to a solid material [AA] for use an an electrolyte for a fuel cell or for a sensor or as a catalyst, each having a polycrystal or single crystal structure, comprising:

(a) a structure of the formula:

$$AF_3$$

wherein A is independently selected from lanthanum, cerium, neodynium, praseodynium, scandium or mixtures thereof, wherein $AF_3$ is a single crystal or a portion thereof;

(b) a structure of the formula:

$$Pb_{1-x}M_xF_{2-x}$$

wherein M is independently selected from potassium, or silver, and x is between about 0.0001 and 0.25;

(c) a structure of the formula:

$$Pb_{1-x}Bi_xF_{2+x}$$

wherein x is defined herein above;

(d) a structure of the formula:

$$A_yB_{1-y}F_{2+y}$$

wherein:
A as defined hereinabove,
B is independently selected from strontium, calcium, barium or magnesium, and y is between about 0.0001 and 1;

(e) a structure of the formula:

$$A_yB_{1-y-z}LiF_{2+y+z}$$

wherein A, B and y are as defined hereinabove, z is between about 0.0001 and 0.10 wherein $y+z$ is less than or equal to 1;

(f) a structure of the formula:

$$N_{1-n-m}U_nCe_mF_{2+2n+m}$$

wherein N is independently selected from calcium, strontium or barium, n is between about 0.0001 and 0.05, and m is between about 0.0001 and 0.35;

(g) a structure of the formula:

$$PbSnF_4$$

with the proviso that $PbSnF_4$ is only useful as a fuel cell electrolyte;

(h) a structure of the formula:

$$KSn_2F_5;$$

(i) a structure of the formula:

$$SrCl_2.KCl;$$

(j) a structure of the formula:

$$LaO_{1-p}F_{1+2p}$$

wherein p is between about 0.0001 and 0.9999;

(k) a structure of the formula:

$$PbSnF_q.PbSnO_r$$

wherein q and r are each independently from between about 0.0001 and 1;

(l) a structure of the formula:

$$(AO_{1.5})_y(GF_2)_{1-y}$$

wherein A is as defined hereinabove, y is between about 0.0001 and 1, and G is independently selected from calcium and magnesium; or (m) a structure of the formula:

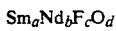

$Sm_aNd_bF_cO_d$ wherein a and b are each independently between about 2.18 and 9.82 and c is between about 12 and 29.45, and d is between about 3.25 and 12, with the proviso that a+b is about 12 and c+2d is about 36.

In another aspect, the present invention relates to a process for the preparation of an electrolyte for a fuel cell or for a sensor, which process comprises:
(a) reacting a structure of material [AA] above in an atmosphere comprising a mixturre of oxygen and water wherein the water is present in between about 1 and 99% by weight at between 100° and 1000° C. for between about 10 and 50 hrs.

In another aspect, the present invention relates to a process for the preparation of an electrolyte for a fuel cell or for a sensor, which process comprises:
(a) subjecting, for instance, about one gram of a structure of material [AA] above to a current of about $10^{-3}$ amperes per square centimeter at a temperature of between 0° and 400° C. for a time sufficient to transmit a certain amount of coulombs equivalent to a product of one Faraday (coulombs/mole) times X where X is between about 0.001 and 1, depending upon the specific material structure.

In another aspect, the present invention relates to a process [BB] for preparing a composite consisting essentially of:

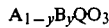

$A_{1-y}B_yQO_3$ having a perovskite or a perovskite-type structure as an electrode catalyst in combination with:

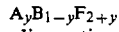

$A_yB_{1-y}F_{2+y}$ as a discontinuous surface coating solid electrolyte wherein A is independently selected from lanthanum, cerium, neodymium, praseodymium, or scandium, B is independently selected from strontium, calcium, barium or magnesium, Q is independently selected from nickel, cobalt, iron or manganese, and y is between about 0.0001 and 1, which process comprises:
(a) obtaining a particulate of:

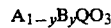

$A_{1-y}B_yQO_3$ wherein A, B and y are defined hereinabove having an average crystal size distribution of between about 50 and 200 Angstroms in diameter and a surface area of between about 10 and 100 meters$^2$/g and formed into a film-like or pellet-like shape having a general thickness of between about 1 and 5 mm, a pore size of between about 25 and 200 Angstroms; and
(b) reacting the particlulate of step (a) with a vapor comprising:

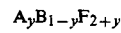

$A_yB_{1-y}F_{2+y}$ wherein A, B and y are defined hereinabove, at about ambient pressure at between about 0° and 1000° C.: for between about 10 and 30 hr. obtain the composite of between about 25 to 1000 microns in thickness; and
(c) recovering the composite of step (b) having multiple interfaces between:

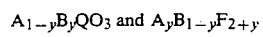

$A_{1-y}B_yQO_3$ and $A_yB_{1-y}F_{2+y}$ said composite having a pore size of between about 25 and 200 Angstroms and a surface area of between about 10 and 100 meters$^2$/gram.

A preferred embodiment in this process [BB] is wherein A is lanthanum, B is strontium, Q is cobalt, and especially where y is about 0.3. Another preferred embodiment of process [BB] is wherein A is selected from cerium or scandium, B is selected from strontium or magnesium, Q is selected from nickel, cobalt or manganese and y is between about 0.2 and 0.4.

In another aspect the present invention relates to the use of the composite of claim 16 selected from electrode/electrolyte for a fuel cell, a sensor, or a contact catalyst for synthesis or degradation.

The use of the composite material of claim 28 as an electrode/electrolyte for a fuel cell or a sensor.

The use of the composite material of claim 30 as an oxygen sensor or a fuel cell.

In another aspect the present invention relates to the process for the generation of electricity, which process comprises:
(a) contacting a solid electrolyte of [AA] above or prepared by process [BB] above with a fuel at between about 0° and 1000° C.

In another aspect the present invention relates to the process described herein wherein the fuel for the fuel cell is selected from hydrogen, hydrazine, ammonia, fossil fuels, separate components of fossil fuels, or mixtures thereof, wherein all fuels have a boiling point at ambient temperature of 250° C. or less. It is especially useful to obtain a fuel cell having an operating temperature between about 10° and 30° C.

In another aspect, the composite material may be prepared by replacing the perovskite-type structure of the process [BB] with a metal-phthalocyanine structure, wherein the metal is selected from iron, cobalt, nickel and the like.

In still another aspect, the perovskite-type electrode (or the metal-phthalocyanine electrode) and the discontinuous fluoride electrolyte of process [BB] are each thin films of between about 1 and 25 microns on a conventional inorganic catalyst support.

BRIEF DESCRIPTION OF THE DRAWINGS

FIG. 1 shows Table 1 as a comparison of various types of fuel cells.

FIG. 4 is at 0.575 volts using Pd/Pt electrodes.

FIG. 5 is a table showing the open circuit voltage ($V_{oc}$) for air, nitrogen, oxygen and hydrogen.

FIG. 7 is a cross section of a solid material composite useful as a solid electrode having a catalyst support, a platinum contact, a solid coating of an electrolyte (e.g., $La_{0.7}Sr_{0.3}F_{2.7}$) with a solid discontinuous coating of a perovskite-type (e.g., $La_{0.7}Sr_{0.3}CoO_3$) or a metal phthalocyanine (Co, Ni, or Fe phthalocyanine) electrode.

FIG. 7A is an enlarged cross section showing the discontinuous nature of the electrolyte in contact with the electrode on the solid support.

DETAILED DESCRIPTION OF THE INVENTION AND PREFERRED EMBODIMENTS

Figure 2:
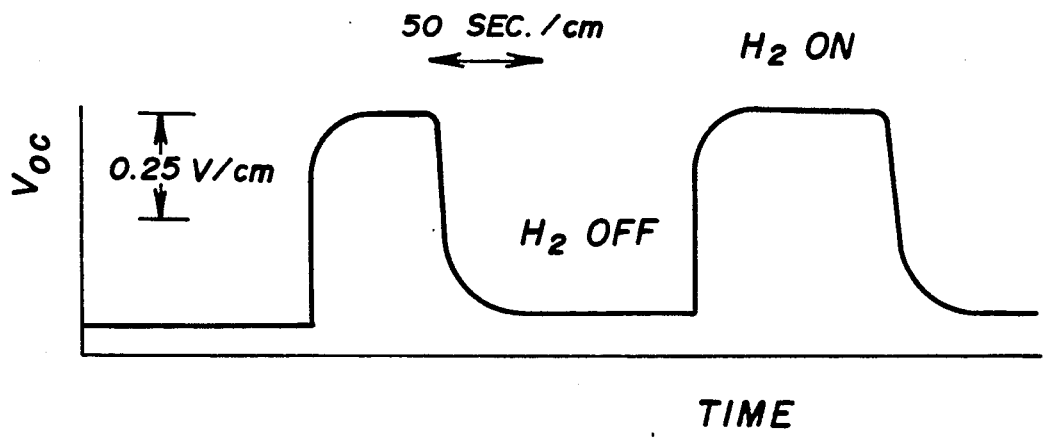
FIG. 2 shows the open circuit voltage ($V_{oc}$) versus time using a single crystal of lanthanum fluoride (LaF$_3$).

In the present invention, lanthanum fluoride is the solid electrolyte of choice for a fuel cell, or a sensor. Its properties are shown below in Table 2.

TABLE 2

PROPERTIES OF $LaF_3$

Crystal structure: hexagonal space group is $P6_3/mcm - D_{6h}^3$ with twelve formula units per cell,
Melting Point: 1493° C.
Density: 5.936,
Dielectric constant: 14 (at 10 MHz),
Thermal conductivity: 0.025 (W cm$^{-1}$ deg$^{-1}$),
Electrical conductivity $\sim 10^{-7} \Omega^{-1}$ cm$^{-1}$ (at 25° C.)
Transmits light from the vacuum ultraviolet into the infrared,
The effective Debye temperature is: +360° K.,
The activation energy for fluorine ion diffusion is $\sim 0.45$ eV,
Activation energy for the formation of defects: $\sim 0.07$ eV,
Birefringence: $\Delta n = 0.006$,
Thermal expansion coefficient: $11 \times 10^{-6}$ cm/cm/°C. (c-axis, 25° C.), a good match is Cu, $LaF_3$ has unique physicochemical properties such as high electrical conductivity and high polarizability at room temperature. The Debye temperature of $LaF_3$ is only 360° K., while its melting point is as high as 1766° K. The observed phenomena appear to be associated with the formation of Schottky defects and with the diffusion of defects has the unusually low value of $\sim 0.07$ eV, and the room temperature Schottky defect density is about $10^{19}$/cm$^3$.

Fluorine in $LaF_3$ usually exists in three magnetically nomequivalent sites. Covalent bonding predominates in two of the sites. In the third site, the fluorines make up a layered array with approximately 60% ionic bonding and about 40% $\pi$-bonding. The high polarizability and high conductivity of $LaF_3$ at room temperature is primarily due to the motion of $F^-$ ions through the latter sites. The relatively small radius of $F^-$ is almost identical with that of the oxide $O^{2-}$ ion (1.25 A); therefore oxide ions ($O^{2-}$ ions) can substitute for the $F^-$ ions in $LaF_3$. It has been confirmed that the oxygen ion transport is through the bulk of a single crystal $LaF_3$ by Auger electron spectroscopy. In other words, the solid electrolyte $LaF_3$ serves as a supporting electrolyte analogous to liquid phase in which oxygen ions can move freely.

Lanthanum Fluoride as a Solid Electrolyte for Fuel Cell

Traditionally $LaF_3$ has been extensively used as a $F^-$ ion selective electrode in electroanalytical chemistry. Recently $LaF_3$ has been applied to a room temperature potentiometric oxygen sensor and to a multifunctional sensor for humidity, temperature, oxygen gas, and dissolved oxygen. However, no disclosure exists concerning the use of $LaF_3$ material as a single crystal as a solid electrolyte in a fuel cell. In earlier investigations, it was determined that polycrystalline lanthanum fluoride as a thin film solid electrode was unreliable and unpredictable. About one of ten electrodes prepared shorted out under laboratory conditions. As is described below, the single crystal lanthanum fluoride solid electrolyte was reliable and predictable.

Figure 3:
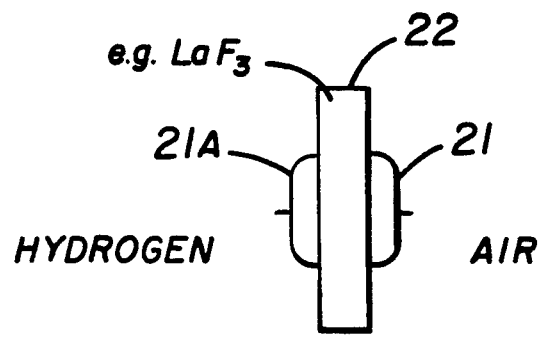
FIG. 3 shows a configuration of a fuel cell using, for instance, a single crystal of thinly-machined and polished lanthanium fluoride.

FIG. 2 illustrates a result on a $LaF_3$ fuel cell. In this case, a single crystal of between about 10 and 100 mils is used. As shown in FIG. 3, one cm diameter single crystal $LaF_3$ with a thickness of 25 mils was used. A comb-shape noble metal (Pt, Au, or Pd) electrode (21+21A) was sputtered on both sides of the $LaF_3$ sample 22. One electrode was exposed to pure hydrogen and the other was exposed to room air. A Pt/Pt system exhibited an open circuit potential ($V_{oc}$) of about 0.6 volts at room temperature. The result was repeatable upon on an on/off cycle of hydrogen. When the Pt/oxygen cathode 21 was replaced by a Pd electrode with a different configuration, $V_{oc}$ was increased to 0.88 volts. However, in either case, the observed short circuit currents were in the order of $10^{-8}$ Amperes. This small amount of current is due to the fact that, in the electrode configuration used in our experiments, the total area of the triple-interface (i.e. gas, electrode catalyst, and solid electrolyte) available for electrochemical reactions was extremely small. Current density is greatly increased when a large surface area platinum black is used as an electrode.

The following electrochemical reactions may take place at each electrode:

Cathode: $O_2 + 4e^- = 2O^{2-}$,

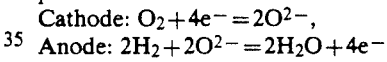
Anode: $2H_2 + 2O^{2-} = 2H_2O + 4e^-$

Effect on $V_{oc}$ of Oxygen Partial Pressure Differences Between Working and Counter Electrodes A study was made to determine how a difference in oxygen partial pressures on either side of the solid electrolyte contributed to the measured $V_{oc}$ values. The relation used was $V_{oc} = RT/4 F \ln P_{O_2}$(At electrode #1)/$P_{O_2}$(At electrode #2) where $P_{O_2}$ stands for partial pressure of oxygen at the electrode specified, R is the universal gas constant, T is the temperature in Kelvin, and F is Faraday's constant.

Figure 4:
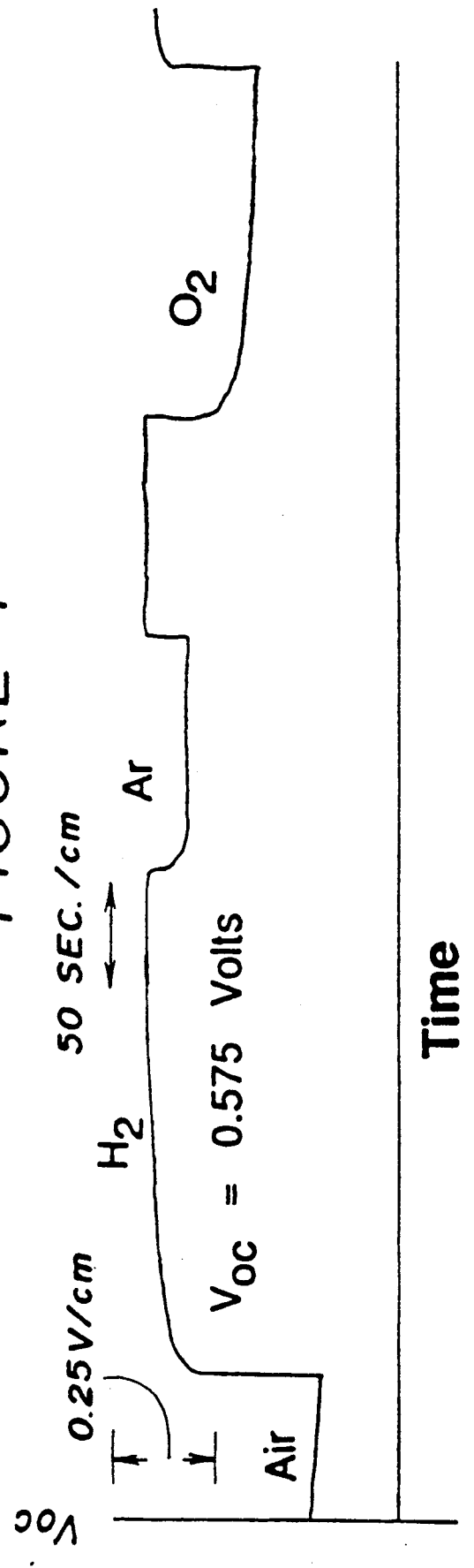
FIG. 4 shows a curve of the open circuit voltage versus time using a single crystal of lanthanum fluoride (LaF$_3$).

However, from the results seen in FIG. 4 and in FIG. 5 (Table 3) the oxygen partial pressure differences do not determine the measured $V_{oc}$ with air at working electrode and oxygen at the counter electrode. This will confirm the result that the observed $V_{oc}$ is indeed due to a fuel cell function.

Those solid materials containing both lanthanum and fluorine (especially structure of formula (a)), are very attractive as solid electrolytes in low temperatures (10° to 30° C.) solid electrolyte of fuel cells.

In preferred embodiments of material [AA] above, each of the structures (a) through (m) are each independently preferred as a solid electrolyte for a fuel cell, a solid electrolyte for a sensor or as a catalyst, espeacially as fuel cell or a sensor.

In a preferred embodiment, the solid material material [AA] of the SUMMARY is selected from structures of formula (a), (b), (d), (e) or (j). In another embodiment the solid material of [AA] of the SUMMARY is selected from structures of formula (a), (b), (f), (h), (j) or (k).

Other preferred embodiments of the solid material include the following:

[1] fuel cell of material [AA] above has a useful operational temperature range of between about 0° and 1000° C. especially wherein the structure in subpart (a) is $AF_3$ wherein A is lanthanum, and also where the operational temperature is between about 15° and 30° C.;

[2] the electrolyte of material [AA] is used in a device as a sensor to detect gases selected from oxygen in the gaseous phase or dissolved in a liquid;

[3] the electrolyte of material [AA] is used for a sensor wherein the sensor has a useful operating range of between about −40° C. to +1000° C.; or

[4] the solid material [AA] above as an electrolyte for a sensor of [AA] above is wherein the oxygen sensor has an operating range of between about 0° C. and 600° C.

In the present invention the solid materials of [AA] are unless otherwise stipulated, individually preferred as a component of a fuel cell, of a sensor or as a catalyst useful in the interconversion formation and degradation of organic compounds, nitrogen-containing compounds and the like.

It is intended that the solid materials described herein for use as solid electrolytes for fuel and for sensors optionally include pretreatment of the surface of the solid, preferably structures of formula (a), especially where A is lanthanum as described herein below.

Pretreatment Using Oxygen Atmosphere

An instrinsic single crystal of $LaF_3$ has a conductivity of $10^{-7}$ ohm$^{-1}$ cm$^{-1}$ (which is mainly due to F$^-$ ions) at room temperature. It is suggested that the oxygen ion conductivity in $LaF_3$ may be increased simply by sintering the crystal in an oxygen gas atmosphere because some of F$^-$ ions may be replaced by $O^{2-}$ ions. Recently, Yamazoe et al., (supra) reported that the response time of $LaF_3$ oxygen sensor was dramatically improved by the treatment of $LaF_3$ in a stream of air containing 15 torr of water vapor at 150° C. for 12 hr. This improvement is presumably due to the formation of a lanthanum oxy-fluoride at the surface (the chemical composition may be written as lanthanum oxyfluoride of the structure (j) in material [AA] above.

In the present invention, the materials described in the Summary of the Invention (and in claim 1) are sintered in an oxygen environment at elevated temperature. The material is placed in an oxygen atmosphere containing from 1 to 99 percent by weight of water. Usually the water present is between about 10 and 30 percent by weight especially about 15 percent by weight. The temperature is usually between about 100° and 1000° C., preferably between about 150° and 600° C., especially between about 200° and 400° C.

Pretreatment using Electrical Polarization

It is also possible to pretreat a solid material [AA] to enhance its ionic conductivity by contacting the material with a polarizing electrical current. Thus, the electrochemical doping (pumping) of oxide ions is achieved by subjecting about 1 gram of the material [AA] to $10^{-3}$ amperes per square centimeter for between about 1 to 25 hr at ambient temperature. Stated in another way about 1 gram of the structure of the material [AA] above is subjected to a certain amount of coulombs equivalent to a product of one Faraday (coulombs/mole) times X where X is between about 0.001 and 1 a depending on the specific material [AA] structure (a) to (m). This electrochemical pumping may be performed between about 0° and 400° C.

An Electrode/Electrolyte Composite

Perovskite-type

In general, the electrocatalysts for the above cited low temperature solid electrolyte fuel cell can be noble metals (e.g. platinum), their alloys or blacks, metalphthalocyanines, transition metal catalysts (e.g. Ni/NiO), and metallic transition metal oxides (e.g. $La_{0.9}Sr_{0.1}MnO_3$).

Particularly, it is of interest to use electronically conductive perovskite-type oxide: e.g.:

$$A_{1-y}B_yQO_3$$

where A, B, Q and y are as defined hereinabove as catalytic electrode materials, especially for the oxygen reaction in conjunction with the lanthanide fluoride solid electrolyte:

$$A_yB_{1-y}F_{2+y}$$

wherein A is: (La, Ce, Nd, Pr or Sc); and B is: (Sr, Ca, Ba or Mg); and y is between about 0.001 and 1.

An example of such a composite electrode/electrolyte system would be: $La_{0.3}Sr_{0.7}CoO_3/La_{0.7}Sr_{0.3}F_{2.7}$. On this interface the electronically conductive phase (electrode: $La_{0.7}Sr_{0.3}F_{2.7}$) exist adjacently to each other and even may be mixed on an atomic-level by sharing La and Sr atoms.

In designing systems of $A_{1-y}B_yQO_3/A_yB_{1-y}F_{2+y}$, one can choose atoms for A and B in such a way that there is a maximum degree of matching in the lattice parameters and thermal coefficients of the two phases. Therefore, the composite system $A_{1-y}B_yQO_3/A_yB_{1-y}F_{y+x}$ can be an ideal site to facilitate the following reaction:

$$O_2 + 4e^- = 2O^{2-},$$

because a well defined, stable atomic-scale three-phase interface (gas, electrode, electrolyte) can be established in the $A_{1-y}B_yQO_3/A_yB_{1-y}F_{2+y}$.

The perovskites useful in this invention may be purchased or may be formed according to the procedures described in the literature e.g., T. Kudo et al., U.S. Pat. No. 3,804,674, which is incorporated herein by reference.

A typical perovskite preparation is described below in Example 2.

Figure 6:
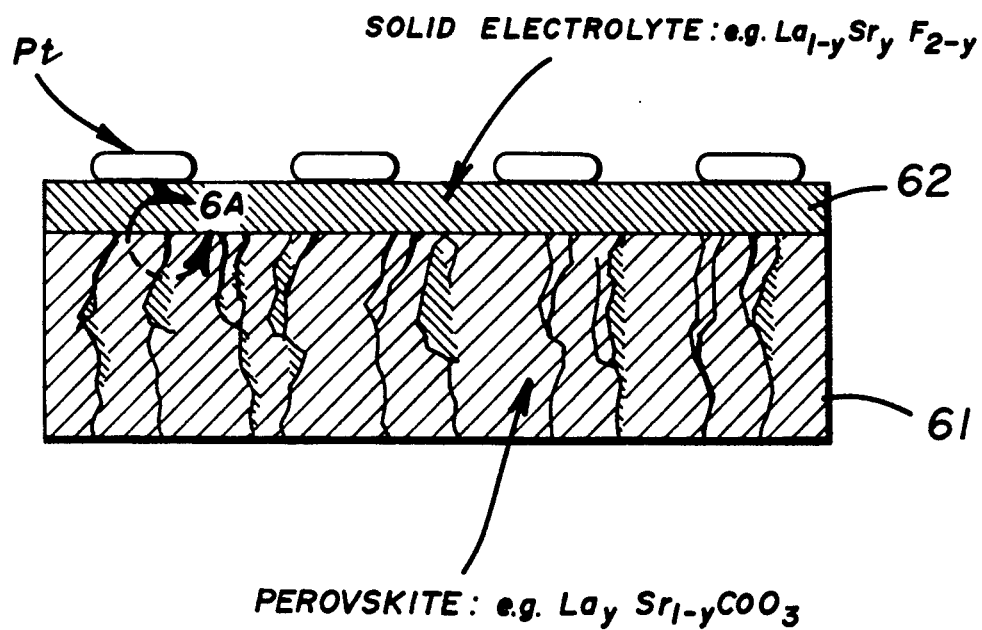
FIG. 6 is a cross section of a solid material composite for solid electrode/electrolyte having a Pt contact, a solid coating of an electrode (e.g. La$_{0.7}$Sr$_{0.3}$F$_{2.7}$ with a perovskite-type electrode (e.g. La$_{0.7}$Sr$_{0.3}$CoO$_3$).
Figure 6A:
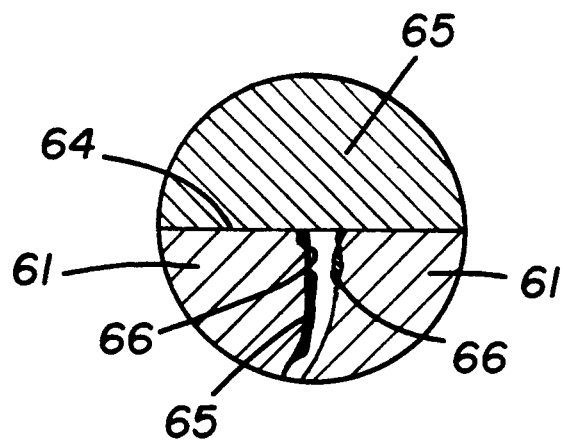
FIG. 6A is an enlarged cross section showing the discontinuous nature of the electrolyte on a pore opening of the porous electrode.

FIG. 6 shows the configuration of a composite for use in a fuel cell. The perovskite substrate (porous oxide) electrode 61 is treated with a vapor to deposit the fluoride electrolyte 62 on the surface. As shown in FIG. 6A fluoride 62 or 65 will enter the pores of the perovskite and also be on the surface 64 of the perovskite in a discontinuous manner. In this way, millions of two material catalytic surface sites 66 are created to facilitate the electrochemical reaction at the intersection of the perovskite 61 and fluoride (62 or 65).

FIG. 7 shows the configuration of a supported composite for use in a fuel cell. The perovskite substrate 71 is spray dried onto an inorganic support 70 such as silica, thoria, zirconia, magnesia, or the like having mechanical stability. The fluoride electrolyte 72 is then vapor deposited on the surface of the perovskite 71. As shown in FIG. 7A the fluoride electrolyte 72 as a vapor enters the pores of the perovskite 71 and the substrate 70 in a discontinuous manner. In this way, millions of two-material catalytic surfaces 74 are created to facilitate the electrochemical reaction at the intersection of the perovskite 71 and fluoride 72.

Metal Phthalocyanines

The present invention also contemplates the use of metal-phthalocyanines in electrode/electrolyte composites. In this embodiment of the invention, the metal-phthalocyanine (Z-phthalocyanine) is used to replace the perovskite-type oxide described above on a weight to weight basis and is then combined with the solid electrolyte as is described above. The metal ions (Z−) preferred include iron, cobalt, nickel and the like.

Typical metal-phthalocyanines in these composites include those described above and, for example, those and similar ones described by K. V. Kordesch in U.S. Pat. No. 3,783,026, which is incorporated herein by reference.

The composites described below in claims 28, 29, 30 or 31 are preferred.

Sensors

The use of the structures disclosed herein are described sensors in analiytical devices to determine components in the vapor phase and also in the liquid phase.

These sensors are preferably useful to analyze oxygen, carbon dioxide, methane, ethane, ethylene, ammonia, hydrogen sulfide or the like. Lanthanum fluoride is preferred to analyze oxygen in a gaseous phase or in a liquid, preferably an aqueous solution.

The range of the analysis may be from between about a part per billion to 10,000 parts per million in the gas phase (usually performed in the potentiometric mode). Even high concentrations of a component, for instance, in the liquid phase determined in the current mode because the proportionality is linear rather than logrithmic.

For the structures defined above in the summary in a preferred embodiment the solid material for use as an electrolyte in a fuel cell or in a sensor or for use as catalyst is selected from structures of (b), (c), (d), (e), (f), (h), (i), (j), (k), (l), or (m). A more preferred embodiment of the solid material is selected from the structures of (b), (c), (d), or (e). Another preferred embodiment of the solid material is selected from the structures of (k), (l) or (m).

The following Examples are intended to be illustrative only and are not to be construed as limiting in any way.

EXAMPLE 1

Formation of Solid Thin Films and Fuel Cell Measurements (aa) As is described in B. C. LaRoy et al., (above, and incorporated herein by reference), lead $_{0.75}$ potassium $_{0.25}$ fluoride $_{1.75}$ ($Pb_{0.75}K_{0.25}F_{1.75}$) is evaporated onto in a thin polycrystalline film onto a substrate to a thickness of 25 mils. Pt black is coated onto the polycrystalline film. One electrode is exposed to pure hydrogen and the other is exposed to room air. This Pt/solid electrode/Pt system is expected to exhibit a useful open circuit, potential ($V_{oc}$) of between about 0.5 and 1.0 volts.

(bb) The procedure of subpart (aa) above is repeated, except that the $Pb_{0.75}K_{0.25}F_{1.75}$ is replaced by an equivalent weight of $Pb_{0.75}Bi_{0.25}F_{1.75}$.

(cc) The procedure of subpart (aa) above is repeated, except that the $Pb_{0.75}K_{0.25}F_{1.75}$ is replaced by an equivalent weight of $La_{0.3}Sr_{0.7}F_{2.3}$.

(dd) The procedure of subpart (aa) above is repeated, except that the $Pb_{0.75}K_{0.25}F_{1.75}$ is replaced by an equivalent weight of $La_{0.4}Sr_{0.5}LiF_{2.5}$.

(ee) The procedure of subpart (aa) above is repeated, except that the $Pb_{0.75}K_{0.25}F_{1.75}$ is replaced by an equivalent weight of $Ca_{0.88}U_{0.02}Ce_{0.1}F_{2.14}$.

(ff) The procedure of subpart (aa) above is repeated, except that the $Pb_{0.75}K_{0.25}F_{1.75}$ is replaced by an equivalent weight of $PbSnF_4$.

(gg) The procedure of subpart (aa) above is repeated, except that the $Pb_{0.75}K_{0.25}F_{1.75}$ is replaced by an equivalent weight of $KSnF_5$.

(hh) The procedure of subpart (aa) above is repeated, except that the $Pb_{0.75}K_{0.25}F_{1.75}$ is replaced by an equivalent weight of $SrCl_2.KCl$.

(ii) The procedure of subpart (aa) above is repeated, except that the $Pb_{0.75}K_{0.25}F_{1.75}$ is replaced by an equivalent weight of $LaO_{0.7}YF_{1.6}$.

(jj) The procedure of subpart (aa) above is repeated, except that the $Pb_{0.75}K_{0.25}F_{1.75}$ is replaced by an equivalent weight of $PbSnF_{0.3}.PbSnO_{0.4}$.

(kk) The procedure of subpart (aa) above is repeated, except that the $Pb_{0.75}K_{0.25}F_{1.75}$ is replaced by an equivalent weight of $(LaO_{1.5})_{0.5}(CaF_2)_{0.5}$.

(ll) The procedure of subpart (aa) above is repeated, except that the $Pb_{0.75}K_{0.25}F_{1.75}$ is replaced by an equivalent weight of $Sm_6Nd_6F_{18}O_9$.

In subparts (bb) to (ll) the fuel cell obtained is expected to generate a useful open circuit potential ($V_{oc}$) of between about 0.5 and 1.0 volts.

EXAMPLE 2

Formation of a Perovskite for an Electrode

A pure lanthanum nickelate crystal is synthesized by a co-precipitation technique. The starting materials are $La(NO_3)_3 0.6\ H_2O$ and $Ni(NO_3)_2 0.6H_2O$ (alternatively acetates and chlorides can be used as the starting materials). The proper amounts of each nitrate required to give the desired stoichiometry are weighed and dissolved in doubly distilled water to remove $Na^+$ and separated quickly by a centrifuge technique at 2000 rpm for 15 min., since $Ni(OH)_2$ tends to dissolve at pH ~ 7. This process is repeated several times. The obtained precipitates are dried in an oven at 100° C. overnight. The dried powder is then put in the furnace at 800° C. for 16 hours in an $O_2$ atmosphere. The electrode is made by pressing the powders into 13 mm diameter pellet (Beckman model K-13 die) at a pressure of 300 kg cm$^{-2}$. The pellet is sintered at 750° C. in an $O_2$ atmosphere for 48 hours and the perovskite pellet is recovered.

A thin film (about 100 micrometers) of $La_{0.5}Sr_{0.5}F_{2.5}$ is prepared on the perovskite layer by conventional vacuum evaporation (LeRoy et al.) using pure materials of lanthanum fluoride and strontium fluoride in a tungsten boat applying a current of about 40 amperes in a high vacuum of about $10^{-7}$ torr. The composite obtained is expected to have a useful open circuit potential of between about 0.5 and 1.0 volts.

EXAMPLE 3

A Porous Substrate-La$_{0.5}$Sr$_{0.5}$CoO$_3$ (film)-La$_{0.5}$Sr$_{0.5}$F$_{2.5}$ (film) by Spray Pyrolysis/Vacuum Evaporation or Reactive Sputtering (aa) A thin layer of a perovskite oxide is prepared on a porous substrate (e.g. alumina, zirconia oxide with pore size of abut 100 A with a thickness 1-2 mm) by a spray pyrolysis. As an example, the 50% Sr doped LaCoO$_3$ is prepared as follows: 8.5 g Sr(NO$_3$)$_2$, 23.3 g Co(NO$_3$)$_2$0.6H$_2$O and 17.81 g La(NO$_3$)$_3$0.6H$_2$O (alternatively acetates and chlorides can be used as the starting materials) are dissolved in distilled water and sprayed onto the hot porous substrate (about 10 cm by 10 cm) at a flow rate of about 10 mL/min. The homogeneous constituent is then decomposed at 250° C., followed by quenching oxygen and heating 500° C., in air for 3 hr. The perovskite catalyst loading should be about 10 mg/cm$^2$. Then, a thin film (about 100 $\mu$m) of La$_{0.5}$Sr$_{0.5}$F$_{2.5}$ is prepared on the perovskite layer by a vacuum evaporation using pure materials of LaF$_3$ and SrF$_2$ in a tungsten boat and applying a current of about 40 Amperes in high vacuum of about $10^{-7}$ torr. Alternatively pure metal targets can be used in a sputtering process in a low pressure fluorine atmosphere (e.g. 10 m torr). The obtained fuel cell is expected to generate an open circuit potential (V$_{oc}$) of between about 0.5 and 1.0 volts. (See FIG. 6, 6A, 7, 7A).

In the above (aa) subpart the reaction is repeated using an equivalent weight of nickel phthalocyanine for the perovskite. The composite formed is expected to have a useful open circuit potential of between about 0.5 and 1.0 volts.

EXAMPLE 4

Formation of a Single Crystal Based Fuel Cell

A single crystal of lanthanum fluoride is pretreated in an oxygen atmosphere of 50% oxygen. The single crystal is cut into slabs and one slab is polished down to a thickness of 100–200 micrometers. A layer of porous platinum black of between 100 and 200 micrometers thickness is coated on opposite faces of the slab. One electrode is exposed to pure hydrogen and the other electrode is exposed to room air. This platinum/solid lanthanum fluoride electrolyte/platinum is expected to exhibit a useful open circuit potential (V$_{oc}$) of between about 0.5 and 1.0 volts.

EXAMPLE 5

LaF$_3$ as a Sensor for Oxygen (a) Lanthanum fluoride, as a portion of a single crystal, is machined and polished to the dimensions of 2 cm in diameter and 100 micrometers in thickness. This disk is placed in an appropriate electrical circuit in an analytical sensing device.

(b) When the sensor is contacted with a mixture of gases containing oxygen, it is expected that it is possible to detect the presence of oxygen between about 0.1 and 10,000 ppm.

(c) When the sensor is contacted with aqueous solution containing oxygen, it is expected that the sensor will detect oxygen between about 0.1 and 10,000 ppm.

(d) The other solid materials of [AA] above (a) through (m) are also expected to be useful sensors for oxygen in the gas phase or the liquid phase.

(e) The composite materials described herein as the single crystal or polycrystal when machined as described in subpart (a) above, are expected to be able to detect oxygen in a gas phase or in an aqueous solution.

While some embodiments of the invention have been shown and described herein, it will become apparent to those skilled in the art that various modifications and changes can be made in the present invention regarding solid materials for use as electrodes (electrolytes in fuel cell applications, in sensor applications and in catalyst applications) without departing from its spirit and scope. All such modifications and changes coming within the scope of the appended claims are intended to be covered thereby.

We claim:

1. The use of a solid material as an electrolyte for a fuel cell or for use as a catalyst, each solid material having a polycrystal or single crystal structure, comprising:

(d) a structure of the formula:

$$A_yB_{1-y}F_{2+y}$$

wherein:
   A is independently selected from lanthanum, cerium, neodymium, praseodymium, scandium or mixtures thereof,
   B is independently selected from strontium, calcium, barium or magnesium, and y is between about 0.0001 and 1;

(e) a structure of the formula:

$$A_yB_{1-y-z}LiF_{i+y+z}$$

wherein A, B and y are as defined hereinabove, z is between about 0.0001 and 0.10;

(f) a structure of the formula:

$$N_{1-n-m}U_nCe_mF_{2+2n+m}$$

wherein N is independently selected from calcium, strontium or barium, n is between about 0.0001 and 0.05, and m is between about 0.0001 and 0.35;

(j) a structure of the formula:

$$LaO_{1-p}F_{1+2p}$$

wherein p is between about 0.1 and 0.3, wherein the solid material as an electrolyte for a fuel cell is a thin layer having one side coated with a noble metal which is in contact with a gaseous fuel for a fuel cell and the other side of the thin solid material for the electrolyte is also coated with a noble metal which is in contact with gaseous oxygen, or air or mixtures thereof.

2. The use of a solid material as an electrolyte for a fuel cell of claim 1 wherein the fuel cell has a useful operational temperature range of between 0° and 1000° C.

3. A process for the pretreatment of an electrolyte for a fuel cell, which process comprises:
   reacting a structure of the formula:

$$A_yB_{1-y}F_{2+y}$$

wherein:
   A is independently selected from lanthanum, cerium, neodynium, praseodymium, scandium or mixtures thereof, B is independently selected from strontium, calcium, barium or magnesium, and y is between about 0.0001 and 1;
a structure of the formula:

$$A_yB_{1-y-z}LiF_{2+y+z}$$

wherein A, B and y are as defined hereinabove, z is between about 0.0001 and 0.10;
a structure of the formula:

$$N_{1-n-m}U_nCe_mF_{2+2n+m}$$

wherein N is independently selected from calcium, strontium or barium, n is between about 0.0001 and 0.05, and m is between about 0.0001 and 0.35; or
a structure of the formula:

$$LaO_{1-p}F_{1+2p}$$

wherein p is between about 0.1 and 0.3 wherein the solid material as an electrolyte for a fuel cell is a thin layer having one side coated with a noble metal which is in contact with a gaseous fuel for a fuel cell and the other side of the thin solid material for the electrolyte is also coated with a noble metal which is in contact with gaseous oxygen, or air or mixtures thereof in an atmosphere comprising a mixture of oxygen and water is present in between about 1 and 99% by weight at between 100° and 1000° C. for between about 10 and 50 hrs.

4. A process for preparing a composite comprising:

$$A_{1-y}B_yQO_3$$

having a perovskite or a perovskite-type structure as an electrode catalyst in combination with $$A_yB_{1-y}F_{2+y}$$

as a discontinuous surface coating solid electrolyte wherein A is independently selected from lanthanum, cerium, neodymium, praseodymium, or scandium, B is independently selected from strontium, calcium, barium, or magnesium, Q is independently selected from nickel, cobalt, iron or manganese, and y is between about 0.0001 and 1, which process comprises:
 (a) obtaining a particulate of:

$$A_{1-y}B_yQO_3$$

wherein A, B, Q and y are defined hereinabove having an average size distribution of between about 50 and 200 Angstroms in diameter;
 (b) contacting the particles of step (a) with a vapor comprising:

$$A_yB_{1-y}F_{2+y}$$

wherein A, B and y are defined hereinabove, at about ambient pressure at between about 0° and 1000° C., for between about 10 and 30 hr to obtain a composite of between about 25 to 1000 microns in thickness;
 (c) recovering the composite of step (b) having multiple interfaces between:

$$A_{1-y}B_yQO_3$$

and $$A_yB_{1-y}F_{2+y}$$

said composite having a pore size of between about 25 and 200 Angstroms and a surface area of between about 10 and 100 meters$^2$/gram.

5. The process of claim 4 wherein A is lanthanum, B is strontium, and Q is cobalt.

6. The process of claim 5 wherein y is about 0.3.

7. The process of claim 4 wherein A is selected from cerium or scandium, B is selected from strontium or magnesium, Q is selected from nickel, cobalt or manganese and y is between about 0.2 and 0.4.

8. The composite obtained by the process of claim 4.
9. The composite obtained by the process of claim 5.
10. The composite obtained by the process of claim 6.
11. The composite obtained by the process of claim 7.
12. The use of a composite as a solid electrolyte or as a catalyst
said composite consisting essentially of $$A_{1-y}B_yQO_3$$

having a perovskite or a perovskite-type structure as a solid electrode catalyst in combination with:

$$A_yB_{1-y}F_{2+y}$$

as a discontinuous surface coating solid electrolyte on the perovskite wherein A is independently selected from lanthanum, cerium, neodymium, praseodymium, or scandium, B is independently selected from strontium, calcium, barium or magnesium, Q is independently selected from nickel, cobalt, iron or manganese, and y is between about 0.0001 and 1, wherein the perovskite or perovskite-type structure has an average size and distribution of between about 50 and 200 Angstroms in diameter; and the composite layer of between about 25 and 1000 microns in thickness;
said composite having multiple interfaces between:

$$A_{1-y}B_yQO_3$$

and $$A_yB_{1-y}F_{2+y}$$

and a pore size of between about 20 and 200 Angstroms and a surface area of between about 10 and 100 meters$^2$/gram.

13. The use of the composite of claim 12 which further includes an inorganic support.

14. A process for the generation of electricity, which process comprises:
contacting one side of the solid material of the formula:

$$A_yB_{1-y}F_{2+y}$$

wherein:
A independently selected from lanthanum, cerium, neodynium, praseodymium, scandium or mixtures thereof, B is independently selected from strontium, calcium, barium or magnesium, and y is between about 0.0001 and 1;
a structure of the formula:

$$A_y B_{1-y-z} Li F_{2+y+z}$$

wherein A, B and y are as defined hereinabove, z is between about 0.0001 and 0.10;
a structure of the formula:

$$N_{1-n-m} U_n Ce_m F_{2+2n+m}$$

wherein N is independently selected from calcium, strontium or barium, n is between about 0.0001 and 0.05, and m is between about 0.0001 and 0.35; or
a structure of the formula:

$$La O_{1-p} F_{1+2p}$$

wherein p is between about 0.1 and 0.3 wherein the solid material as an electrolyte for a fuel cell is a thin layer having one side coated with a noble metal which is in contact with a gaseous fuel for a fuel cell and the other side of the thin solid material for the electrolyte is also coated with a noble metal which is in contact with gaseous oxygen, or air or mixtures thereof and a first electrode with a fuel at between about 0° and 1000° C., and
contacting the second side of the solid electrolyte and second electrode with air, oxygen, or mixtures thereof.

15. The process of claim 14 wherein the fuel for the fuel cell is selected from hydrogen, hydrazine, ammonia, fossil fuels, separate components of fossil fuels, or mixtures thereof, wherein all fuels have a boiling point at ambient pressure of 250° C. or less.

16. The process of claim 15 wherein the operating temperature is between about 10° and 30° C.

17. A process for the pretreatment of an electrolyte for a fuel cell which process comprises:
subjecting the equivalent of about one gram of a solid material of a structure of the formula:

$$A_y B_{1-y} F_{2+y}$$

wherein:
A is independently selected from lanthanum, cerium, neodynium, praseodynium, scandium or mixtures thereof,
B is independently selected from strontium, calcium, barium or magnesium, and y is between about 0.0001 and 1;
a structure of the formula:

$$A_y B_{1-y-z} Li F_{2+y+z}$$

wherein A, B and y are as defined hereinabove, z is between about 0.0001 and 0.10;
a structure of the formula:

$$N_{1-n-m} U_n Ce_m F_{2+2n+m}$$

wherein N is independently selected from calcium, strontium or barium, n is between about 0.0001 and 0.05, and m is between about 0.0001 and 0.35; or
a structure of the formula:

$$La O_{1-p} F_{1+2p}$$

wherein p is between about 0.1 and 0.3 wherein the solid material as an electrolyte for a fuel cell is a thin layer having one side coated with a noble metal, which is in contact with a gaseous fuel for a fuel cell and the other side of the thin solid material for the electrolyte is also coated with a noble metal which is in contact with gaseous oxygen, or air or mixtures thereof to a current of about $10^{-3}$ amperes per square centimeter for a time sufficient to transmit a certain amount of coulombs equivalent to a product of one Faraday (coulombs/mole) times X where X is between about 0.001 and 1 at a temperature of between about 0° and 400° C.

* * * * *